United States Patent
Lloyd et al.

(10) Patent No.: US 10,158,433 B2
(45) Date of Patent: Dec. 18, 2018

(54) SYSTEM AND METHOD FOR CHARACTERIZATION OF MULTI-ELEMENT ANTENNA

(71) Applicant: Rohde & Schwarz GmbH & Co. KG, Munich (DE)

(72) Inventors: Gareth Lloyd, Munich (DE); Markus Reil, Munich (DE); Mahmud Naseef, Munich (DE)

(73) Assignee: Rohde & Schwarz GmbH & Co. KG, Munich (DE)

( * ) Notice: Subject to any disclaimer, the term of this patent is extended or adjusted under 35 U.S.C. 154(b) by 0 days.

(21) Appl. No.: 15/385,565

(22) Filed: Dec. 20, 2016

(65) Prior Publication Data

US 2018/0074104 A1  Mar. 15, 2018

(30) Foreign Application Priority Data

Sep. 12, 2016 (EP) .................................... 16188305

(51) Int. Cl.
| | |
|---|---|
| *H04B 1/00* | (2006.01) |
| *H04B 17/10* | (2015.01) |
| *H01Q 1/24* | (2006.01) |
| *H01Q 21/24* | (2006.01) |
| *H04B 17/16* | (2015.01) |
| *H01Q 3/24* | (2006.01) |

(Continued)

(52) U.S. Cl.
CPC ........... *H04B 17/102* (2015.01); *G01R 27/28* (2013.01); *G01R 29/10* (2013.01); *H01Q 1/243* (2013.01); *H01Q 3/24* (2013.01); *H01Q 21/00* (2013.01); *H01Q 21/245* (2013.01); *H04B 17/101* (2015.01); *H04B 17/16* (2015.01); *G01N 1/00* (2013.01); *H04B 1/00* (2013.01); *H04B 17/0085* (2013.01); *H04B 17/19* (2015.01); *H04B 2201/00* (2013.01)

(58) Field of Classification Search
CPC ........ H04B 1/00; H04B 2201/00; G01N 1/00; G01N 2201/00; G01R 1/00
See application file for complete search history.

(56) References Cited

U.S. PATENT DOCUMENTS

| | | | |
|---|---|---|---|
| 7,098,847 B2 * | 8/2006 | Li | H01Q 3/267 342/174 |
| 2002/0089447 A1 * | 7/2002 | Li | H01Q 1/246 342/368 |

(Continued)

OTHER PUBLICATIONS

Bailey, "5G Outlook Test and Measurement Aspects", http://cwbackoffice.co.uk/Presentation/RTSS%2003.02.15%20Rohde&Schwarz.pdf, XP002767221, Feb. 3, 2015.

(Continued)

*Primary Examiner* — Jermele M Hollington
*Assistant Examiner* — Temilade Rhodes-Vivour
(74) *Attorney, Agent, or Firm* — Potomac Technology Law, LLC (57) ABSTRACT

A system for measuring or characterizing a multi-element antenna having at least two antenna elements comprises a vector network analyzer with at least two input/output ports. Each input/output port of the vector network analyzer is connected to one antenna element of the multi-element antenna. The vector network analyzer has generator means for generating waves at each of its input/output ports, which are coherent to each other.

11 Claims, 9 Drawing Sheets

(51) Int. Cl.
*H01Q 21/00* (2006.01)
*G01R 27/28* (2006.01)
*G01R 29/10* (2006.01)
G01N 1/00 (2006.01)
H04B 17/00 (2015.01)
H04B 17/19 (2015.01)

(56) References Cited

U.S. PATENT DOCUMENTS

| | | | |
|---|---|---|---|
| 2006/0009162 A1* | 1/2006 | Tan | H01Q 3/267 455/67.11 |
| 2007/0194776 A1* | 8/2007 | Bossche | G01R 27/28 324/76.22 |
| 2013/0343490 A1* | 12/2013 | Wertz | H04B 17/21 375/340 |
| 2016/0043778 A1 | 2/2016 | Sikina et al. | |
| 2016/0095171 A1* | 3/2016 | Chaimov | H05B 6/6447 219/704 |
| 2016/0174456 A1* | 6/2016 | Barychev | A01C 1/025 47/14 |
| 2016/0269093 A1 | 9/2016 | Seol et al. | |
| 2017/0336454 A1 | 11/2017 | Hinotani et al. | |

OTHER PUBLICATIONS

EPO, "Extended European Search Report", EPO Application No. 16188305.3, dated Feb. 24, 2017.
Naseef, et al., "Characterizing Active Phased Array Antennas", Rohde & Schwarz Application Note, 8.2016-1MA248_2e, https://www.rohde-schwarz.com/appnote/1MA248, Aug. 2016.

* cited by examiner

SYSTEM AND METHOD FOR CHARACTERIZATION OF MULTI-ELEMENT ANTENNA

PRIORITY

This application claims the benefit of the earlier filing date under 35 U.S.C. § 120 of European Patent Application No. EP16188305.3 (filed 2016 Sep. 12), the entirety of which is incorporated by reference herein.

FIELD OF THE INVENTION

The invention concerns a system and a method for characterization of multi-element antennas.

BACKGROUND

Millimeter-wave bands are of increasing interest for the satellite industry and potential 5G bands. Multi-element antennas for 5G applications make use of these high frequencies to incorporate a large count of radiating elements. These antenna arrays are essential for beamforming operations that play an important part in such next generation networks.

Presently one is unable to fully and directly measure and characterize a multi-element antenna, for example, one used in beamforming applications. Many parameters must be estimated or calculated from a basic measurement on one element. A theoretical calculation is not a measurement verification.

Characterization of a multi-element antenna generally requires at least two procedures: Measurements based on S-parameters (e.g., return loss, cross-coupling between elements, etc.), and Pattern Measurement, including Beam Steering and complex Beam Formation.

For pattern measurement, the prior art is to excite a single antenna element and measure the single-element beam pattern. Such an approach is described in the Rohde & Schwarz Application Note "Characterizing Active Phased Array Antennas," August 2016, which can be obtained from the website https://www.rohde-schwarz.com/appnote/1MA248, and is incorporated by reference herein. The Beam Steering weightings and Complex Beam Formation are then calculated theoretically, but are not measured and therefore not verified.

Especially in multi-element arrays with few elements, the theoretical calculations can be heavily in error. Generally, this is because the extreme elements behave differently.

SUMMARY OF EXAMPLE EMBODIMENTS

Embodiments of the present invention advantageously address the foregoing by providing an apparatus and method for measuring or characterizing a multi-element antenna, while avoiding the connection and disconnection of the signal source. Further, the following descriptions introduce some of the fundamental theory behind beamforming antennas, and describe calculation methods for radiation patterns, and show a number of real world measurement results for linear arrays.

According to a first aspect of the invention, a system for measuring and/or characterizing a multi-element antenna having at least two antenna elements comprises a vector network analyzer with at least two input/output ports. Each input/output port of the vector network analyzer is connected to one antenna element of the multi-element antenna. The vector network analyzer has generator means for generating waves at each of its input/output ports, which are coherent to each other.

According to a second aspect of the invention, a method for measuring and/or characterizing a multi-element antenna comprising at least two antenna elements uses a vector network analyzer with at least two input/output ports and comprise the steps: connecting each input/output port of the vector network analyzer to one antenna element of the multi-element antenna and generator waves at each of input/output port of the vector network analyzer, which are coherent to each other, by generator means of the vector network analyzer.

With the provided apparatus and method only a single connection of a device under test (DUT) is required. A single connection of measurement equipment is made, rather than using different measurement instruments and successively disconnecting and reconnecting them.

A direct measurement and verification of the beam steering and complex beam formation can be made. The exact antenna element weightings is then known exactly, rather than theoretically calculated.

For complex Beam Forming, for example, two specific directions having a maximum rejection between them, etc., weightings may be precisely verified with measurement, instead of erroneously estimated from a calculation.

According to example embodiments, a signal source having multiple connected, but independently controlled, outputs is employed. The plurality of outputs are connected to the inputs of a multi-element antenna DUT. These are optionally connected to a turntable device or other device for precise mechanical movement.

Separated by some distance is a receiver antenna, which is optionally connected to a device for precise mechanical movement, whose output is connected to the input of a signal analyzer (e.g., a spectrum analyzer, power sensor or similar).

Further, the component devices may be time-synchronized.

The outputs of the signal source have their parameters swept (e.g., frequency, relative amplitude, relative phase). Relative physical alignment of the DUT antenna and receive antenna are also swept in a known, controlled and synchronized fashion. These are the independent variables.

The signal analyzer is responsible for measuring received signal parameters (e.g., received signal strength). This represents the dependent variable.

The measurement results may then be post-processed and optimum operating values extracted.

Beam Steering, i.e. directive gain maximized in a specific direction, weightings may be precisely verified with measurement, instead of erroneously estimated from a calculation.

For Complex Beam Forming, e.g. two specific directions having a maximum rejection between them, etc., weightings may be precisely verified with measurement, instead of erroneously estimated from a calculation.

With the above method and apparatus only a single connection of the DUT is required. Ideally, the signal source is capable of S-parameter measurements. A minimum of one antenna must be capable of having its physical position varied.

Still other aspects, features, and advantages of the present invention are readily apparent from the following detailed description, simply by illustrating a number of particular embodiments and implementations, including the best mode contemplated for carrying out the present invention. The present invention is also capable of other and different embodiments, and its several details can be modified in various obvious respects, all without departing from the spirit and scope of the present invention. Accordingly, the drawing and description are to be regarded as illustrative in nature, and not as restrictive.

BRIEF DESCRIPTION OF THE DRAWINGS

Embodiments of the present invention are illustrated by way of example, and not by way of limitation, in the figures of the accompanying drawings, in which like reference numerals refer to similar elements, and in which.

DETAILED DESCRIPTION OF EXAMPLE EMBODIMENTS

An apparatus and method for measuring or characterizing a multi-element antenna, while avoiding the connection and disconnection of the signal source, are described. In the following description, for the purposes of explanation, numerous specific details are set forth in order to provide a thorough understanding of the invention. It is apparent, however, that the invention may be practiced without these specific details or with an equivalent arrangement. In other instances, well-known structures and devices are shown in block diagram form in order to avoid unnecessarily obscuring the invention.

Current cellular 4G networks face a multitude of challenges. Soaring demand for mobile high resolution multimedia applications brings these networks ever closer to their practical limits.

5G networks are envisioned to ease the burden on the current infrastructure by offering significantly higher data rates through increased channel bandwidths. Considering the shortage of available frequencies traditionally used for mobile communications, mm-wave bands became a suitable alternative. The large bandwidth available at these frequencies helps to offer data rates that satisfy 5G demands.

However, the mobile environment at these mm-wave bands is far more complex than at the currently used frequencies. Higher propagation losses that greatly vary depending on the environment require an updated network infrastructure and new hardware concepts.

Beamforming antenna arrays will play an important role in 5G implementations since even small handsets can accommodate a large number of antennas at mm-wave frequencies. Aside from a higher directive gain, these antenna types offer complex beamforming capabilities. This allows to increase the capacity of cellular networks by improving the signal to interference ratio (SIR) through direct targeting of user groups. The narrow transmit beams simultaneously lower the amount of interference in the radio environment and make it possible to maintain sufficient signal power at the receiver terminal at larger distances in rural areas.

The following provides an overview of the beamforming technology including signals, antennas and current transceiver architectures. Furthermore, simulation methods for linear antenna arrays are introduced and compared to actual measurement results.

Beamforming in general works with simple continuous wave (CW) signals as well as with complex modulated waveforms. Candidate waveforms for 5G are a current research topic, since many of today's implementations suffer great disadvantages at millimeter wave bands.

This part will first introduce phase coherent signal generation before giving an overview of the most important propagation characteristics of these signals.

Figure 1:
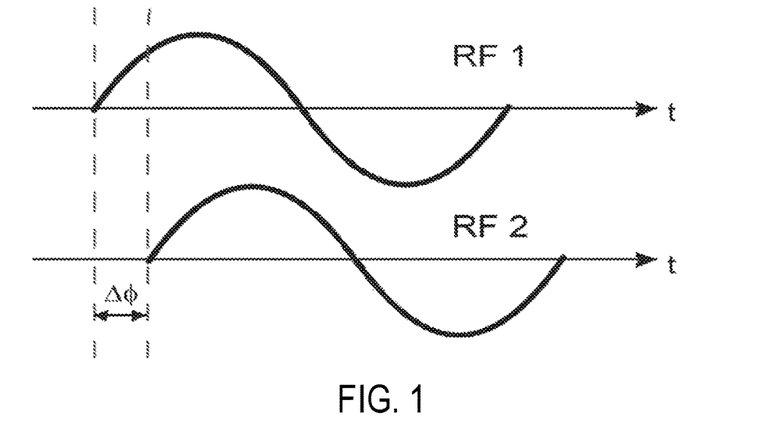
FIG. 1 shows phase coherent signals with phase offset.

An important prerequisite for every beamforming architecture is a phase coherent signal. This term means that there is a defined and stable phase relationship between all RF carriers. A fixed delta phase between the carriers, as shown in FIG. 1, can be used to steer the main lobe to a desired direction.

Phase coherence can be achieved by coupling multiple signal generators via a common reference (i.e. 10 MHz). A closer inspection of the instantaneous differential phase ("delta phase") of these RF signals shows instability due to phase-noise of the two synthesizers, "weak" coupling at 10 MHz and a long synthesis chain up to the radio frequency (RF) output, and temperature differences which cause a change in the effective electrical length of some synthesizer components.

Because of the dominance of the second factor, the only way to stabilize the phase between two signal generators is to use a common synthesizer/LO source. This measure simultaneously eliminates the first factor.

In a test and measurement environment, there are two ways of generating multi-channel phase coherent signals. One way is by using a daisy chain of signal generator. In this Specification, however, the second method is discussed, that is using the VNA (vector network analyzer).

All signals radiated from any kind of antenna share the same basic characteristics. Multipath fading and delay spread significantly reduce the capacity of a cellular network. Congestion of the available channels and co-channel interference further reduce the practical network capacity.

In Free Field Attenuation, electromagnetic waves are attenuated while travelling from the transmitter to the receiver. The free field attenuation describes the attenuation which the signal will suffer due to the distance between the two stations.

The Friis formula determines the free field attenuation, where $P_{r,dB}$ is the received power level in dB, $P_{t,dB}$ the transmitted power, and $G_{r,dB}$ and $G_{t,dB}$ the receive and transmit antenna gain in dBi, as follows:

$$P_{r,dB} = P_{t,dB} + G_{t,dB} + G_{r,dB} + 20\log_{10}\left(\frac{\lambda}{4\pi R}\right) \quad (1)$$

Figure 2A:
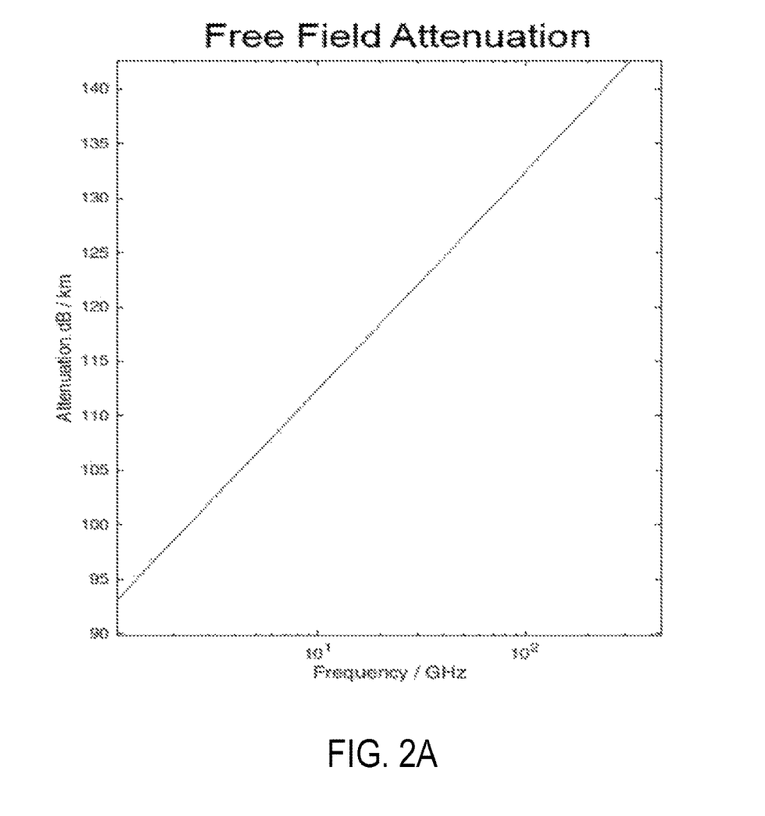
FIG. 2A and FIG. 2B show attenuation due to atmospheric gases.
Figure 2B:
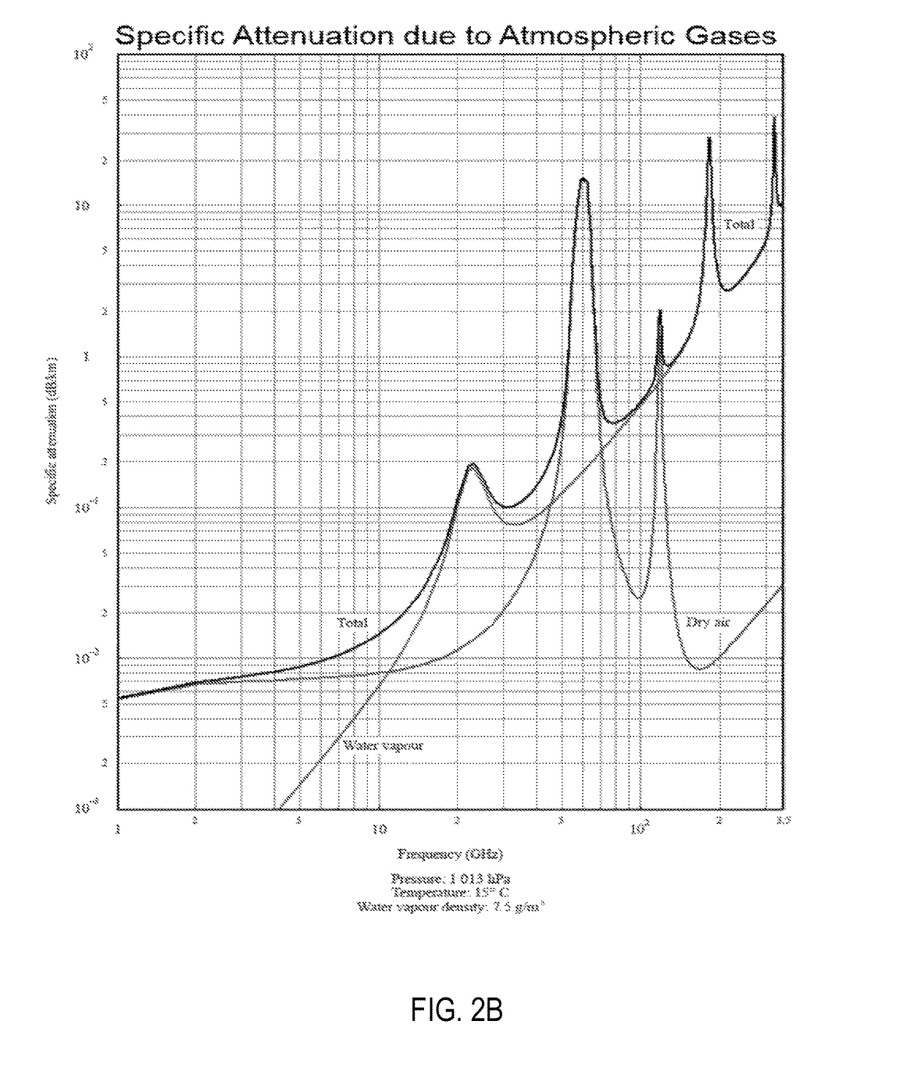

FIG. 2A illustrates the free field attenuation over a large frequency band. Even in case of a perfect line of sight (LoS) transmission, there are many different factors that additionally affect the magnitude of the received signal. As shown in FIG. 2B, the resulting overall attenuation varies greatly depending on the frequency and radiation environment.

If the fading occurs, the phase shift in multipath signals is non-constant due to the time variant nature of the channel. The time-dependent received multipath signal, where the complex values $a_n(t)$ and $e^{-j\theta_n(t)}$ describe the change in amplitude and phase for the transmit path n, can be expressed as follows:

$$r(t) = s(t) \sum_{n=1}^{N} |a_n(t)| e^{-j\theta_n(t)} \quad (2)$$

The signals add up constructively or destructively depending on the current phase shift. The received signal consists of a multitude of scattered components making it a random process. Based on a sufficient amount of scattered components, this can be seen as a complex Gaussian process. This results in the creation of small fade zones in the coverage area which is called Rayleigh-Fading.

A special case of fading is the phase cancellation, which occurs when multipath signals are 180° out of phase from each other. The cancellation and thus the attenuation of the signal depends largely on the amplitude and phase balance. A 30 dB difference for example corresponds approximately to a 0.1 dB and 1.0 degree matching error.

The effect of Delay Spread is also due to the multipath nature of signal propagation. It describes the difference between the time of arrival of the earliest and latest significant multipath component. Typically the earliest component is the LoS transmission. In case of large delay spreads the signal will be impaired by inter-symbol interferences which dramatically increase the bit error rate (BER).

Modern beamforming antenna architectures can help to mitigate these problems by adapting to the channel. This way, delayed multipath components can be ignored or significantly reduced through beam steering. Antennas that are designed to adapt and change their radiation pattern in order to adjust to the RF environment are called active phased array antennas.

Millimeter-wave bands potentially enable high bandwidths. To date, the limited use of these high frequencies is a result of adverse propagation effects in particular due to obstacles in the LoS. Several transceiver architectures have been developed to compensate these issues by focusing the received or transmitted beams in a desired direction. All these solutions make use of smaller antenna element sizes due to higher carrier frequencies that enable the construction of larger antenna arrays.

Figure 3:
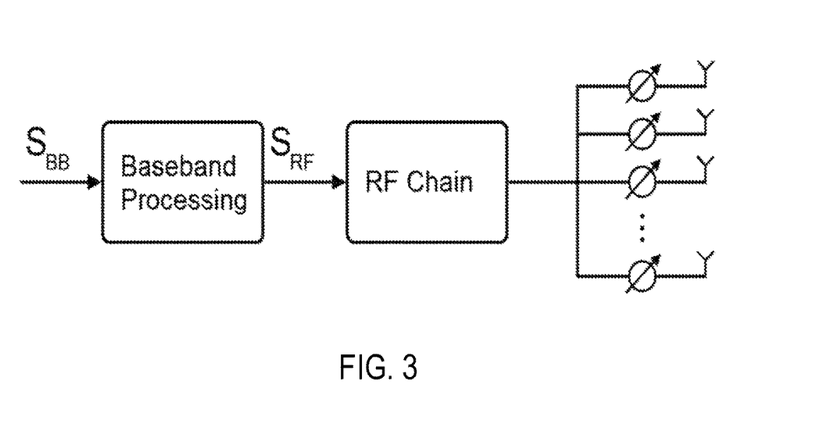
FIG. 3 shows analog beamforming architecture.

Usually two variables are used for beamforming: Amplitude and phase. The combination of these two factors is used to improve side lobe suppression or steering nulls. Phase and amplitude for each antenna element n are combined in a complex weight wn. The complex weight is then applied to the signal that is fed to the corresponding antenna FIG. 3 shows a basic implementation of an analog beamforming transmitter architecture. This architecture consists of only one RF chain and multiple phase shifters that feed an antenna array.

The steering is usually carried out with a selective RF switch and fixed phase shifters. The basics of this method are still used to date, albeit with advanced hardware and improved precoding algorithms. These enhancements enable separate control of the phase of each element. Unlike early, passive architectures the beam can be steered not only to discrete but virtually any angle using active beamforming antennas. True to its name, this type of beamforming is achieved in the analog domain at RF frequencies or an intermediate frequency.

This architecture is used today in high-end millimeter-wave systems as diverse as radar and short-range communication systems like IEEE 802.11ad. Analog beamforming architectures are not as expensive and complex as the other approaches described in this paper. On the other hand implementing a multi-stream transmission with analog beamforming is a highly complex task.

Figure 4:
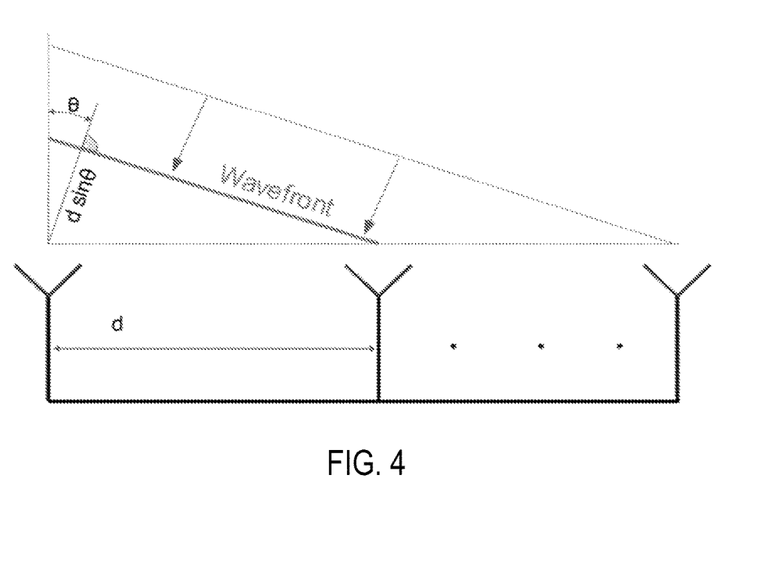
FIG. 4 shows additional travel distance when signal arrives off boresight.

In order to calculate the phase weightings, a uniformly spaced linear array with element spacing d is assumed. Considering the receive scenario shown in FIG. 4, the antenna array must be in the far field of the incoming signal so that the arriving wave front is approximately planar. If the signal arrives at an angle θ off the antenna boresight, the wave must travel an additional distance d*sinθ to arrive at each successive element as illustrated in FIG. 4. This translates to an element specific delay which can be converted to a frequency dependent phase shift of the signal, which can be expressed as follows:

$$\Delta\varphi = \frac{2\pi d \sin\theta}{\lambda} \quad (3)$$

The frequency dependency translates into an effect called beam squint. The main lobe of an antenna array at a defined frequency can be steered to a certain angle using phase offsets calculated with the equation (3). If the antenna elements are now fed with a signal of a different frequency, the main lobe will veer off by a certain angle. Since the phase relations were calculated with a certain carrier frequency in mind, the actual angle of the main lobe shifts according to the current frequency. Especially radar applications with large bandwidths suffer inaccuracies due to this effect.

Equation (3) can be converted to a frequency independent term by using time delays instead of frequency offsets, as follows:

$$\Delta t = \frac{d * \sin\theta}{c} \quad (4)$$

This means that the frequency dependency is eliminated if the setup is fitted with delay lines instead of phase shifters.

The performance of the analog architecture can be further improved by additionally changing the magnitude of the signals incident to the radiators.

While analog beamforming is generally restricted to one RF chain even when using large-number antenna arrays, digital beamforming in theory supports as many RF chains as there are antenna elements. If suitable precoding is done in the digital baseband, this yields higher flexibility regarding the transmission and reception. The additional degree of freedom can be leveraged to perform advanced techniques like multi-beam MIMO. These advantages result in the highest theoretical performance possible compared to other beamforming architectures.

Figure 5:
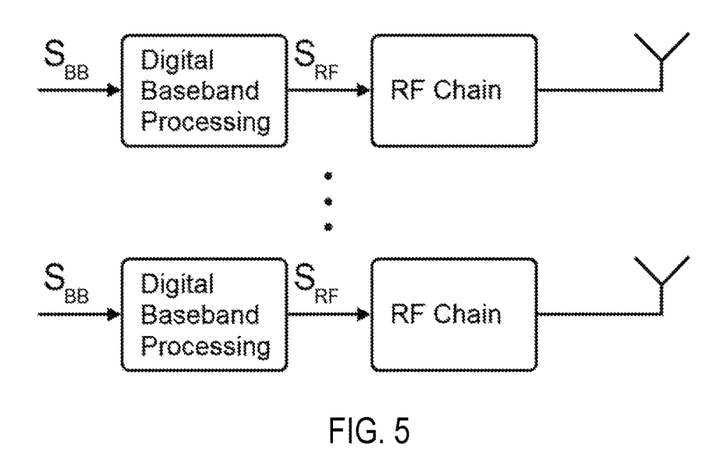
FIG. 5 shows digital beamforming architecture.

FIG. 5 illustrates the general digital beamforming transmitter architecture with multiple RF chains.

Beam squint is a well-known problem for analog beamforming architectures using phase offsets. This is a serious drawback considering current 5G plans to make use of large bandwidths in the mm-wave band. Digital control of the RF chain enables optimization of the phases according to the frequency over a large band.

Nonetheless, digital beamforming may not always be ideally suited for practical implementations regarding 5G applications. The very high complexity and requirements regarding the hardware may significantly increase cost, energy consumption and complicate integration in mobile devices. Digital beamforming is better suited for use in base stations, since performance outweighs mobility in this case.

Hybrid beamforming has been proposed as a possible solution that is able to combine the advantages of both analog and digital beamforming architectures. First results from implementations featuring this architecture have been presented in prototype level.

A significant cost reduction can be achieved by reducing the number of complete RF chains. This does also lead to lower overall power consumption. Since the number of converters is significantly lower than the number of antennas, there are less degrees of freedom for digital baseband processing. Thus the number of simultaneously supported streams is reduced compared to full blown digital beamforming. The resulting performance gap is expected to be relatively low due to the specific channel characteristics in millimeter-wave bands.

Figure 6:
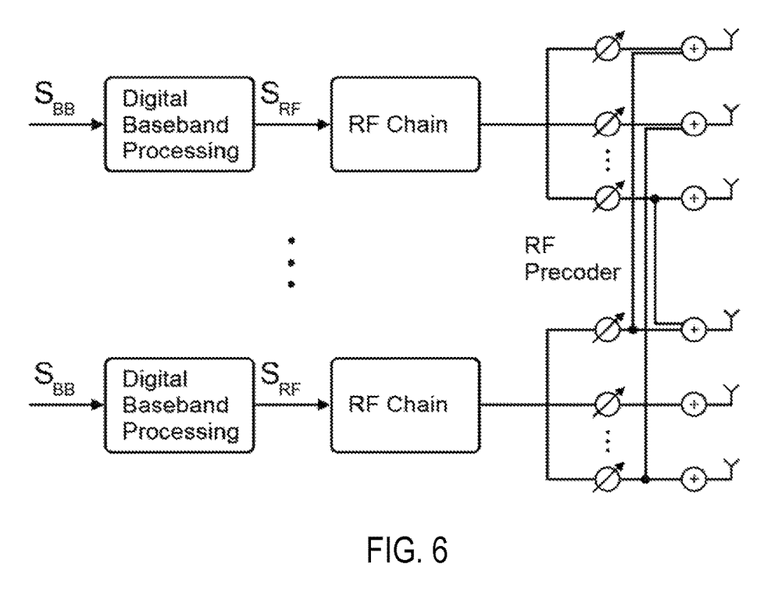
FIG. 6 shows hybrid beamforming architecture.

The schematic architecture of a hybrid beamforming transmitter is shown in FIG. 6. The precoding is divided between the analog and digital domains. In theory, it is possible that every amplifier is interconnected to every radiating element.

The following consists of two sections. The first introduces basic theory while the second section demonstrates the application of these formulas by means of simulated antenna array measurements.

Figure 7:
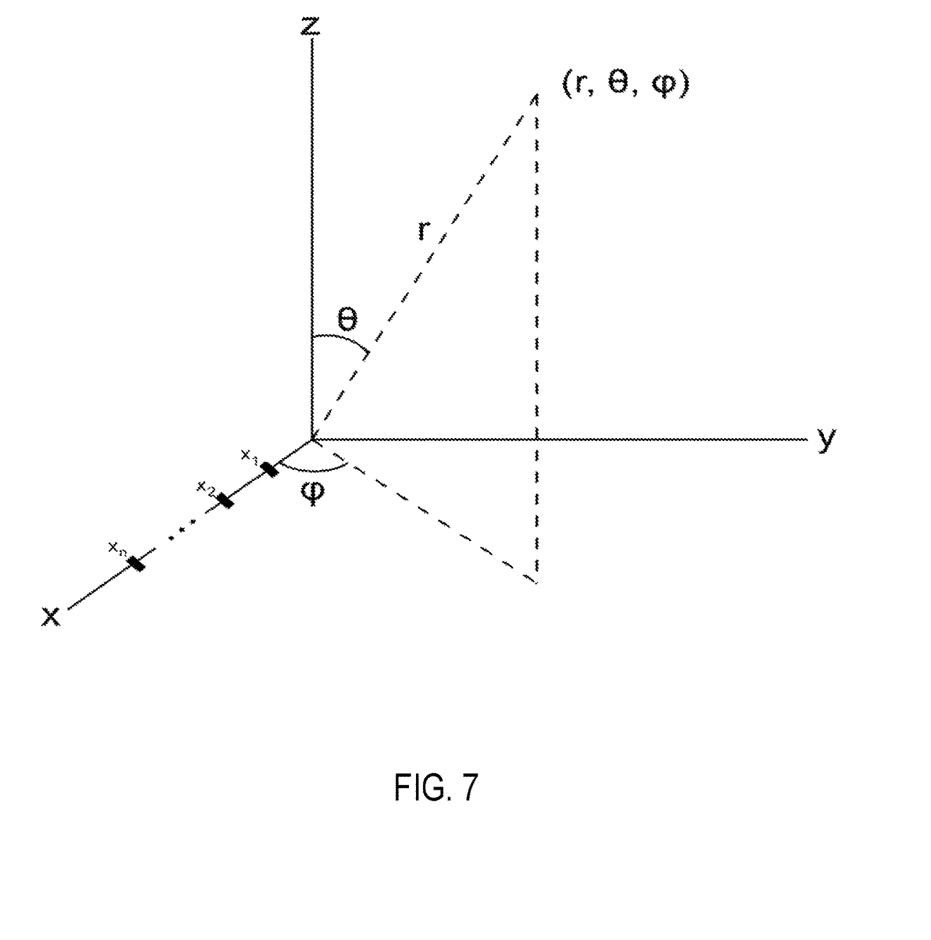
FIG. 7 shows a linear antenna array.

In this part, a linear antenna array with n equally spaced isotropic radiating elements is assumed. These elements can be imagined being placed along the x-axis of a spherical coordinate system, as shown in FIG. 7.

In the case of beamforming antennas, the distance d between the elements should not exceed the wavelength λ to avoid the occurrence of unwanted grating lobes. Equation (5) shows that the element spacing has a great effect on the targeted observation angle, where the location $\theta_r$ of the unwanted grating lobe r is defined by λ, d and the angle of the signal $\theta_0$:

$$\theta_r = \arcsin\left(\pm \frac{\lambda * r}{d} + \sin\theta_0\right); r = 0, 1, 2 \ldots \quad (5)$$

The radiation pattern $F_{array}$ of a linear antenna array can be approximated by multiplying the array factor $AF_{array}$ with the element radiation pattern $F_{element}$ that is considered equal for all elements assuming a large enough array, as follows:

$$F_{array}(\theta,\phi) = F_{element}(\theta,\phi) * AF_{array}(\theta,\phi) \quad (6)$$

If the number of antenna elements is small, the assumption of equal radiation patterns does not hold. The outer elements may deviate by a large degree from the pattern of the other antennas, which cannot be neglected in case of only a few elements. Thus the equation (6) is only applicable for coarse approximation in this case. Mutual coupling and losses in the elements are not considered in this equation, too. These effects contribute to a modified beam pattern manifested in for example increased side lobe levels.

Aside from the element radiation pattern $F_{element}$, the array factor $AF_{array}$ is required to calculate $F_{array}$ according to equation (6). The linear array factor depends on the wavelength λ, the angle direction θ, the distance d between the elements and the number of elements N, as follows:

$$AF_{array}(\theta, \phi) = \sum_{n=1}^{N} a_n e^{jnkd \sin\theta} e^{-j\Delta\varphi}; k = 2 * \frac{\pi}{\lambda} \quad (7)$$

The complex weighting introduced before can be set using equation (7). The amplitude weights are applied per element by the factor $a_n$. The angle $\Delta\varphi$ calculated with the basic beam steering formula (3) can be used to steer the beam to an arbitrary angle.

While the phase offsets of the antenna elements are generally used to determine the angle of the main lobe, the amplitude weighting provides means to modify the beam width and side lobe levels. In case of unity amplitude weights ([1, 1, 1, 1]), the main beam width is smallest.

Decreasing the amplitude levels of the outside elements results in an increased main beam width. If the weights of the outside elements approach zero ([0, 1, 1, 0]), the radiation pattern is approximately equal to a two element array with the same dimensions. The side lobe levels are usually controlled by applying window functions. Every change of the weights leads to a change in the radiation pattern, while each window has its own set of advantages and drawbacks.

Non-equal amplitude weightings are an important instrument for discriminating between two directions. A small trade-off in terms of directive gain for an intended user may result in a much larger rejection of unintended signals.

The effects on the simulated array of using measured data for the element radiation pattern $F_{element}$ will first be introduced. Afterwards, the actual over-the-air (OTA) measurement results obtained from an antenna scan measurement are shown in order to complement the theoretic calculations.

Figure 8:
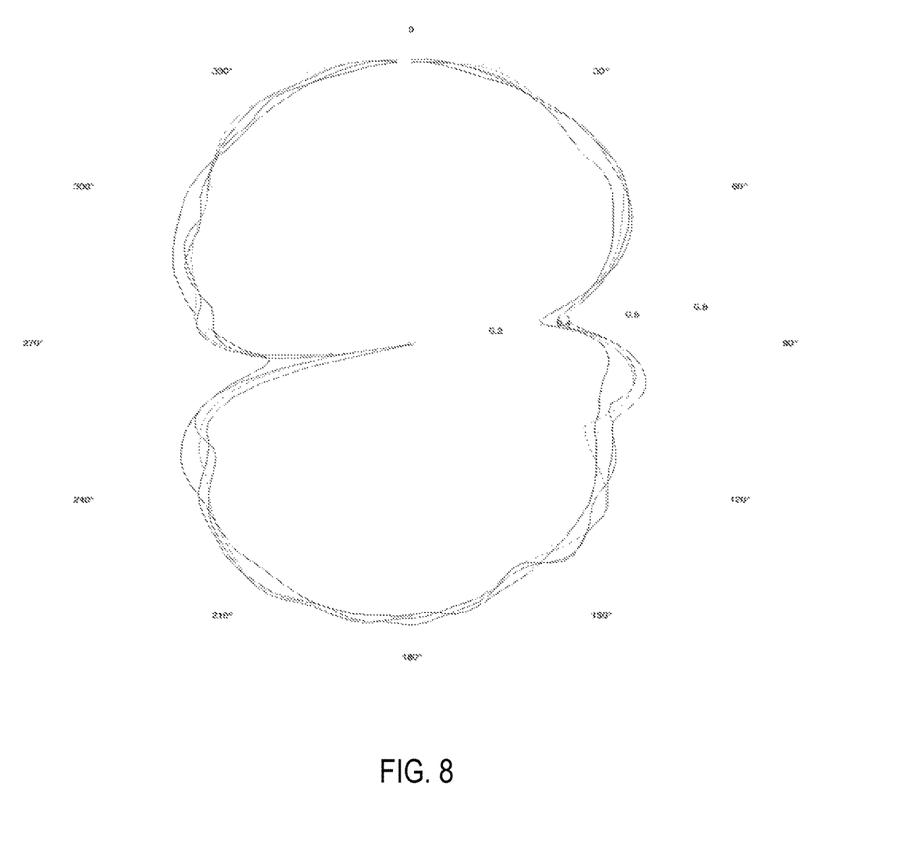
FIG. 8 shows an antenna element radiation pattern.

The antenna used is a linear array consisting of four elements with equidistant spacing. FIG. 8 shows the superimposed, normalized radiation patterns of all elements of the antenna at 28 GHz. The measurements were conducted separately, meaning the other elements were inactive and terminated.

Since the patterns are approximately equal, (6) can be used to get an estimate of the antenna radiation pattern. The element radiation pattern $F_{element}$ used for obtaining the radiation pattern $F_{array}$ was determined by calculating the mean value of all four patterns shown in FIG. 8. $F_{element}$ was measured within a range of 24 GHz to 30 GHz, thus providing a huge database for a comprehensive comparison. This simulation shows that the antenna was optimized for 28 GHz.

The measurement can be made, for example, using an R&S® ZVA 67 network analyzer with four independent sources. This instrument provides phase coherent signal output comparable to a digital beamforming architecture as introduced before.

Figure 9:
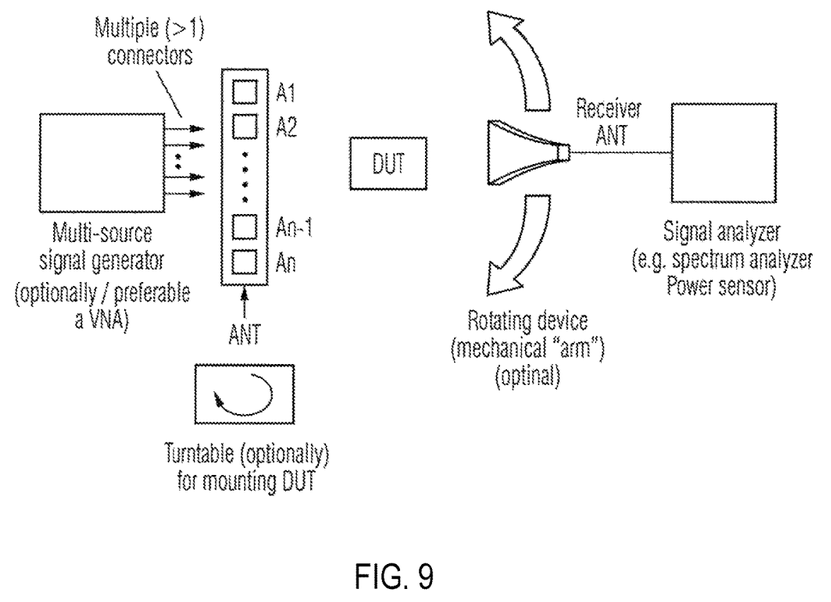
FIG. 9 shows a first example measurement setup according to embodiments of the present invention.

FIG. 9 shows a first embodiment of a setup of the inventive measurement system, according to example embodiments of the present invention. A multi-wave signal generator, which is preferably a vector network analyzer VNA, is connected to a multi-element antenna ANT, which is in connection with the device under test (DUT) in the present case. The multi-element antenna ANT comprises several antenna elements A1, A2, . . . , An−1, An. The DUT is in the vicinity of the multi-element antenna ANT and is addressed over the air by the antenna elements A1 to An. In the embodiment shown in FIG. 9, the multi-element antenna ANT is rotatable for mounting the DUT. However, it might also be, that the multi-element antenna ANT itself is the DUT. However, this is only an optional configuration. In the configuration shown in FIG. 9 there is a separate receiver antenna which can be fixed but preferably is rotatable around one, two or three axis in space. The receiver antenna is connected to a signal analyzer, for example a spectrum analyzer or a power sensor.

Figure 10:
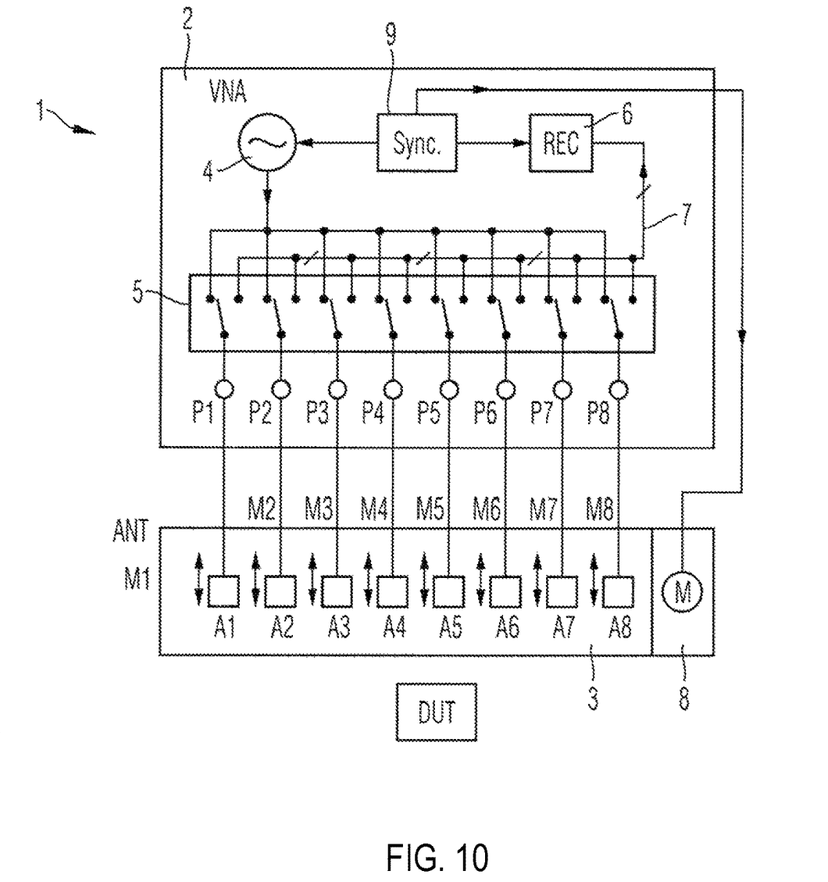
FIG. 10 shows a second example measurement setup according embodiments of the present invention.

FIG. 10 shows a second embodiment of the inventive system 1, according to example embodiments of the present invention. Also here a vector network analyzer VNA is used. The vector network analyzer has several input/output ports P1, P2, P3, P4, P5, P6, P7, P8. This means that, in the shown embodiment, the network analyzer 2 has eight ports.

However, the invention is not limited to this configuration. The vector network analyzer 2 might also have only four ports or even only two ports. It can also have significantly more than eight ports.

Each input/output port P1 to P8 of the vector network analyzer 2 is connected to one antenna element A1, A2, A3, A4, A5, A6, A7, A8 of the multi-element antenna 3. By way of example, there is one antenna element A1 to A8 for each of the input/output ports. However, it might also be that one port serves more than one antenna element or that one of the ports of the network analyzer 2 is not connected to any of the antenna elements of the multi-element antenna 3.

The vector network analyzer 2 has generator means 4, for example a phase-locked-loop (PLL) synthesizer, which is connected to each of the input/output ports P1 to P8 via switching means 5. The vector network analyzer 2 also has receiver means 6 which are also connected via the switching means 5 to the input/output ports P1 to P8. In the shown embodiment each port P1 to P8 is switchable between the generator means 4 and the receiver means 6. However, this is not necessarily the case. It might also be that only some of the ports P1 to P8 are switchable. The switching means 5 might be configured in a manner that each port P1 to P8 can individually be switched either to the generator means 4 and/or to the receiving means 6. For example, a switching is possible, such that only one or only a few of the ports (e.g., P1 to P4) are connected to the generator means 4 where the other ports (e.g., P5 to P8) are all connected to the receiver means 6. The receiver means 6 should have an individual line to each of the ports which is demonstrated in FIG. 10 by a bus line 7 which might have eight individual wires in the present case.

The multi-element antenna 3 has manipulator means 8 for manipulating or moving in a linear and/or a rotational manner either all of the antenna elements A1 to A8 or each antenna element A1 to A8 individually. By way of example, the manipulation means may consist of motors, step motors, varactors, solenoids or other mechanical positioning mechanisms known in the art.

The vector network analyzer 2 also comprises synchronization means 9 for at least synchronizing the generator means 4 and the receiver means 6. By way of example, synchronization is done in a manner that there is coherence between generating the waves and receiving the waves. By way of further example, synchronization can also be done in a manner that the start and end of the measurement period is synchronized or in a manner that triggering is synchronized.

In one embodiment, the synchronization means 9 also synchronizes the motion of the manipulation means 8. Synchronization can, for example, be done in manner that the antenna elements A1 to A8 are only moved between the individual measurement periods and are not moved during active measurement periods.

Figure 11:
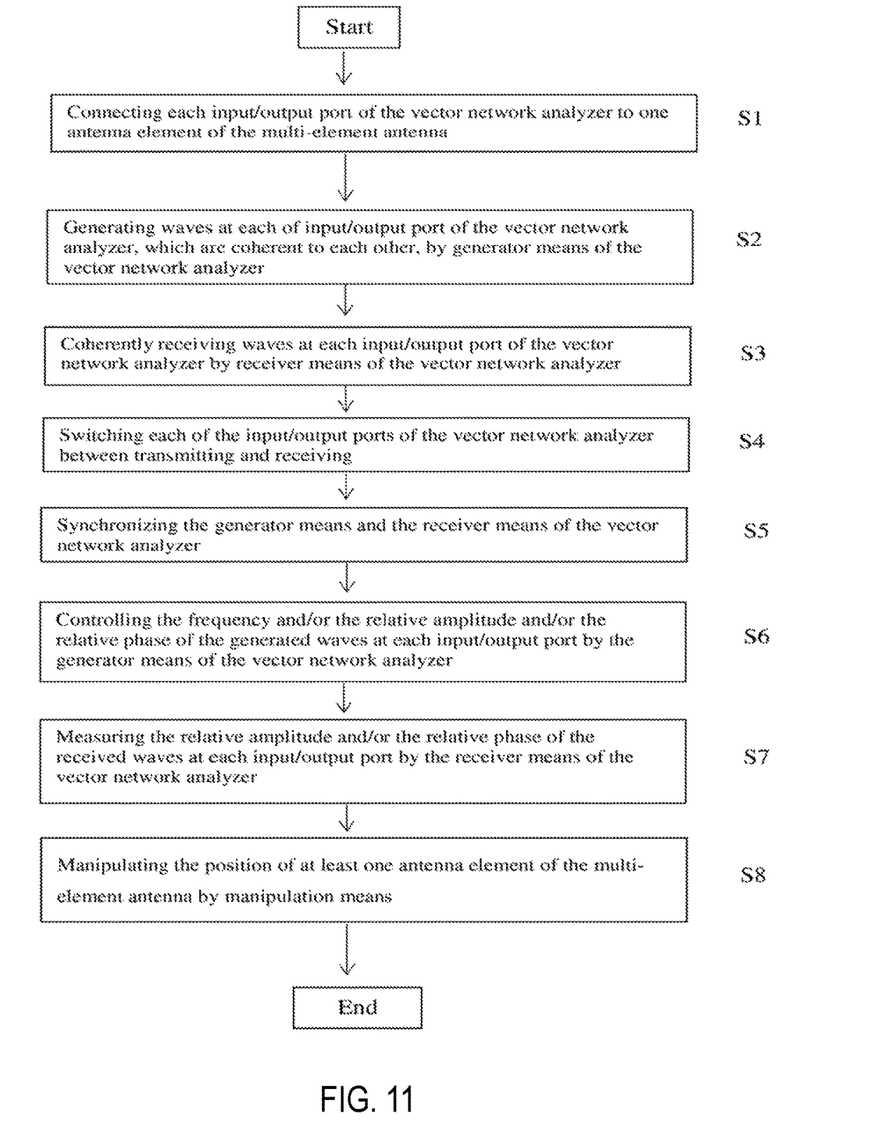
FIG. 11 shows a method for measuring or characterizing a multi-element antenna according to embodiments of the present invention.

FIG. 11 shows a flow chart of an inventive method for measuring and characterizing the multi-element antenna 3, according to example embodiments of the present invention. In Step S1, each input/output port of the vector network analyzer is connected a respective antenna element of the multi-element antenna. In Step S2, a signal generator means of the vector network analyzer generates waves at each input/output port of the vector network analyzer, which are coherent to each other. In Step S3, a receiver component or means of the vector network analyzer coherently receives the waves at each input/output port of the vector network analyzer. At Step S4, each of the input/output ports of the vector network analyzer is switched between transmitting and receiving. At Step S5, the signal generator means and the receiver means of the vector network analyzer are synchronized. At Step S6, one or more of the frequency, the relative amplitude and the relative phase of the generated waves at each input/output port is/are controlled by the signal generator means of the vector network analyzer. At Step S7, one or more of the relative amplitude and the relative phase of the received waves at each input/output port is/are measured by the receiver means of the vector network analyzer. At Step S8, the position of at least one antenna element of the multi-element antenna is manipulated or moved via a manipulation device or means.

The signal generator means 4 and the receiver means 6 may be comprised in a common housing along with the synchronization means 9 and the switching means 5. The measured results may be post-process and defined operating values may be extracted. For example, S-parameters can be extracted. By the exact alignment of the antenna element A1 to A8, the relative physical alignment of the DUT antenna and/or receiving antenna is known and can be controlled and synchronized with the receiver means 6 and/or the generator means 4.

It is already widely accepted that beamforming will play an important role in the implementation of next generation networks. Many 5G topics are still subjects of ongoing research, but the general direction taken by the industry includes small as well as large beamforming arrays, the latter in part only made feasible by the shorter wavelengths encountered in millimeter-wave bands.

This Specification introduces some aspects of beamforming technology from basic signal propagation to the implementation of uniform linear array architecture. Other configurations as described before can also be used. All features described in the description, all features claimed in the claims and all features shown in the drawings can be combined.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

What is claimed is:

1. A system comprising:
   a multi-element antenna comprising at least two antenna elements; and
   a vector network analyzer comprising (i) a plurality of input/output ports, wherein each input/output port is connected to a respective one of the antenna elements of the multi-element antenna, (ii) a signal generator configured to generate waves at each of the input/output ports, wherein the waves are coherent to each other, (iii) a receiver configured to coherently receive the waves at each of the input/output ports, and (iv) a synchronization device configured to synchronize the signal generator and the receiver; and
   wherein the system is configured to measure or characterize the multi-element antenna.

2. The system of claim 1, wherein the vector network analyzer further comprises a switch configured to switch each of the input/output ports of the vector network analyzer between the signal generator for transmitting and the receiver for receiving.

3. The system of claim 1, wherein the signal generator of the vector network analyzer is further configured to control one or more of a frequency, a relative amplitude and a relative phase of the generated waves at each of the input/output ports.

4. The system of claim 1, wherein the receiver of the vector network analyzer is further configured to measure one or more of a relative amplitude and a relative phase of the received waves at each of the input/output ports.

5. The system of claim 1, further comprising:
   a mechanical device configured to change a position of one or more of the antenna elements of the multi-element antenna.

6. The system of claim 5, wherein the mechanical device and the signal generator are synchronized.

7. A method comprising:
   generating, by a signal generator of a vector network analyzer, waves at each of a plurality of input/output ports of the vector network analyzer, wherein the waves are coherent to each other, and wherein each input/output port is connected to a respective antenna element of a multi-element antenna;
   receiving, by a receiver of the vector network analyzer, the waves at each input/output port of the vector network analyzer;
   synchronizing the signal generator and the receiver of the vector network analyzer; and
   measuring or characterizing the multi-element antenna.

8. The method of claim 7, further comprising:
   a switch configured to switch each of the input/output ports of the vector network analyzer between the signal generator for transmitting and the receiver for receiving.

9. The method of claim 7, further comprising:
   controlling one or more of a frequency, a relative amplitude and a relative phase of the generated waves at each of the input/output ports.

10. The method of claim 7, further comprising:
    measuring one or more of a relative amplitude and a relative phase of the waves at each of the input/output ports.

11. The method of claim 7, further comprising:
    changing a position of one or more of the antenna elements of the multi-element antenna.

* * * * *